United States Patent [19]

Kimura et al.

[11] Patent Number: 4,620,868
[45] Date of Patent: Nov. 4, 1986

[54] N-[(4,6-DIMETHOXYPYRIMIDIN-2-YL)AMINOCARBONYL]-3[HALO-SUBSTITUTED ETHENYL (OR PROPENYL)]-2-THIOPHENESULFONAMIDES USEFUL AS HERBICIDES

[75] Inventors: Fumio Kimura; Takahiro Haga; Kazuyuki Maeda; Kouji Hayashi; Toshio Seki; Tsunezo Yoshida, all of Shiga, Japan

[73] Assignee: Ishihara Sangyo Kaisha, Ltd., Osaka, Japan

[21] Appl. No.: 683,219

[22] Filed: Dec. 18, 1984

[30] Foreign Application Priority Data

Dec. 27, 1983 [JP] Japan .................. 58-247518
Mar. 15, 1984 [JP] Japan .................. 59-50092
Mar. 16, 1984 [JP] Japan .................. 59-51582

[51] Int. Cl.$^4$ .............. A01N 43/02; C07D 239/02
[52] U.S. Cl. ..................... 71/90; 71/92; 71/93; 544/212; 544/213; 544/320; 544/331
[58] Field of Search ............ 544/320, 331; 71/90, 71/92, 93

[56] References Cited
U.S. PATENT DOCUMENTS

| 4,120,691 | 10/1978 | Levitt | 71/90 |
| 4,169,719 | 10/1979 | Levitt | 71/92 |
| 4,398,939 | 8/1983 | Levitt | 71/90 |
| 4,441,910 | 4/1984 | Shapiro | 71/90 |
| 4,461,640 | 7/1984 | Levitt | 71/92 |
| 4,521,597 | 6/1985 | Kristinsson et al. | 544/320 |

Primary Examiner—Donald G. Daus
Assistant Examiner—Cecilia Shen
Attorney, Agent, or Firm—Sughrue, Mion, Zinn, Macpeak & Seas

[57] ABSTRACT

Novel substituted thiophenesulfonamide compounds useful as herbicides which are represented by the following formula, and salts thereof:

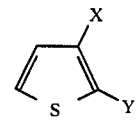

wherein either one of X and Y is an ethenyl or propenyl group having all hydrogen atoms replaced by chlorine atoms and/or fluorine atoms, and the other is the group

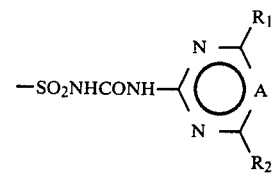

(wherein $R_1$ and $R_2$ are each a methyl or methoxy group, and A is =N— or =CH—).

12 Claims, No Drawings

N-[(4,6-DIMETHOXYPYRIMIDIN-2-YL)AMINOCARBONYL]-3[HALO-SUBSTITUTED ETHENYL (OR PROPENYL)]-2-THIOPHENESULFONAMIDES USEFUL AS HERBICIDES

BACKGROUND OF THE INVENTION

The present invention relates to novel substituted thiophenesulfonamide compounds, salts thereof, herbicides containing the same, and a process for preparing the same. The thiophenesulfonamide compounds of the present invention substituted by an ethenyl or propenyl group having all hydrogen atoms replaced by chlorine atoms and/or fluorine atoms, and the salts of such thiophenesulfonamide compounds are both novel. U.S. Pat. No. 4,398,939 and Japanese Unexamined Published Application No. 24383/82 show thiophenesulfonamide compounds substituted by an alkenyl group having 3 carbon atoms (propenyl group). These compounds have different chemical structures from the compounds of the present invention in that in the latter compounds, i.e., all hydrogen atoms are replaced by chlorine atoms and/or fluorine atoms.

SUMMARY OF THE INVENTION

The present invention provides substituted thiophenesulfonamide compounds of formula (I):

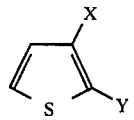

(I)

wherein either one of X and Y is an ethenyl or propenyl group having all hydrogen atoms replaced by chlorine atoms and/or fluorine atoms, and the other is the group

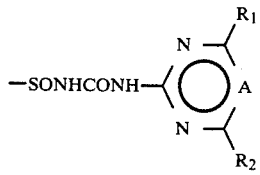

(wherein $R_1$ and $R_2$ are each a methyl or methoxy group, and A is =N— or =CH—). The present invention also provides salts of such compounds and herbicides containing such compounds or salts thereof, as well as a process for preparing said compounds.

DETAILED DESCRIPTION OF THE INVENTION

Illustrative ethenyl and propenyl groups in formula (I) wherein all hydrogen atoms are replaced by chlorine atoms and/or fluorine atoms include 2-chloro-1,2-difluoroethenyl, 1,2,2-trifluoroethenyl and 1,2,3,3,3-pentafluoro-1-propenyl, with 2-chloro-1,2-difluoroethenyl and 1,2,3,3,3-pentafluoro-1-propenyl being preferred. Particularly preferred compounds of formula (I) are such that the ethenyl or propenyl group having all hydrogen atoms replaced by chlorine atoms and/or fluorine atoms is bonded to the thiophene nucleus at 3-position whereas the substituted aminosulfonyl moiety is bonded to the same nucleus at 2-position. Of a substituted pyrimidine or substituted triazine bonded to the ureylene group, the substituted pyrimidine is more preferable. The substituted thiophenesulfonamide compounds of the present invention may form salts with various substances such as alkali metals (e.g., sodium and potassium), alkaline earth metals (e.g., magnesium and calcium), and amines (e.g., dimethylamine and triethylamine).

The compounds of formula (I) may be prepared by either one of the following methods.

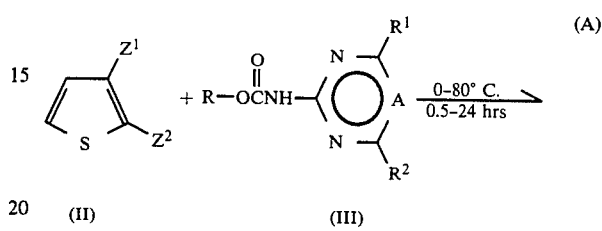

(A)

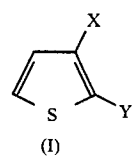

(I)

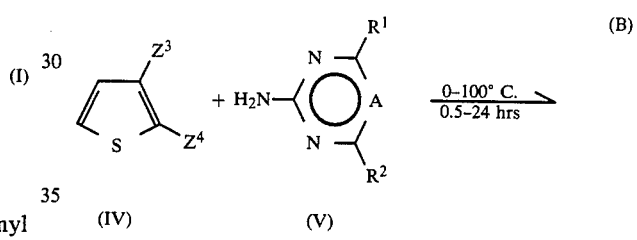

(B)

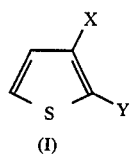

(I)

(wherein one of $Z^1$ and $Z^2$ is an aminosulfonyl group and the other is an ethenyl or propenyl group having all hydrogen atoms replaced by chlorine atoms and/or fluorine atoms; one of $Z^3$ and $Z^4$ is an isocyanatosulfonyl group and the other is a substituted ethenyl or propenyl group as defined above; R is an alkyl, alkenyl or phenyl group; A, X, Y, $R^1$ and $R^2$ are the same as defined above).

The reactions shown above may be performed in the presence of a solvent. Illustrative solvents include aromatic hydrocarbons such as benzene, toluene, xylene and chlorobenzene; cyclic or acyclic aliphatic hydrocarbons such as chloroform, carbon tetrachloride, methylene chloride, dichloroethane, hexane and cyclohexane; ethers such as diethyl ether, methyl ethyl ether, dioxane, and tetrahydrofuran; ketones such as acetone, methyl ethyl ketone and methyl isobutyl ketone; nitriles such as acetonitrile, propionitrile and acrylonitrile; and aprotic polar solvents such as dimethyl sulfoxide and sulfolane.

In order to promote reaction (A), 1,8-diazabicyclo(5,4,0)-7-undecene may be added. In order to promote reaction (B), 1,4-diazabicyclo(2,2,2)octane may be added as a catalyst.

The compound of formula (II) that is used in reaction (A) as the starting material may be prepared by one of the following methods:

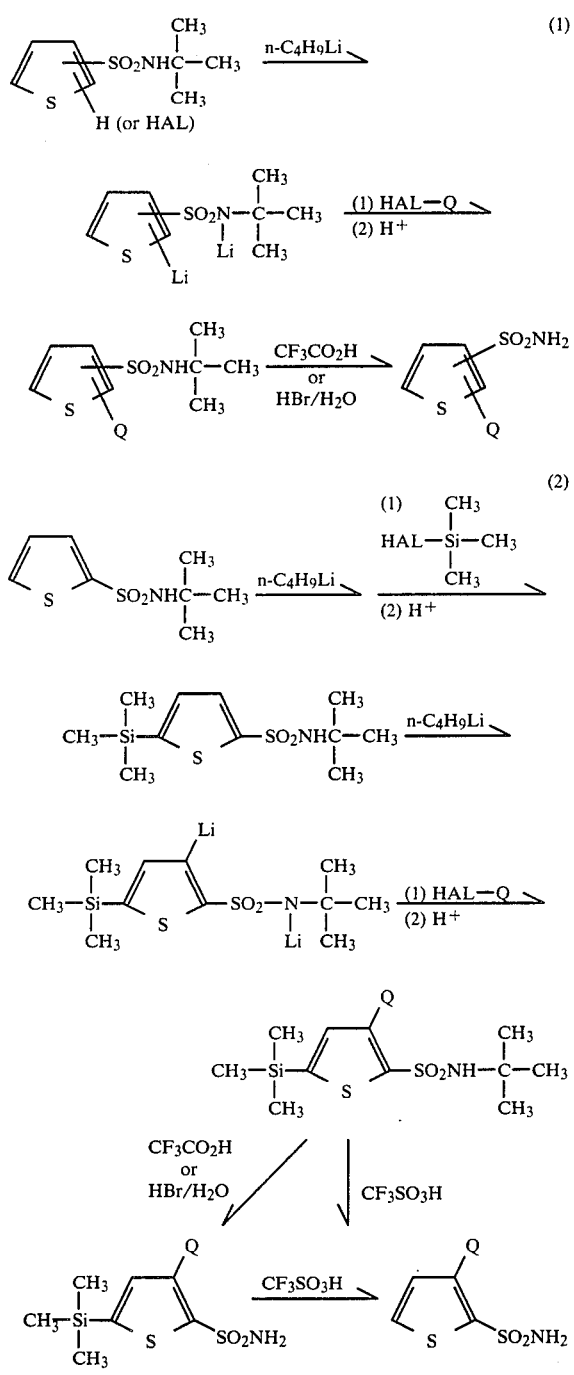

The compound of formula (IV) that is used in reaction (B) as the starting material may be prepared by the following method:

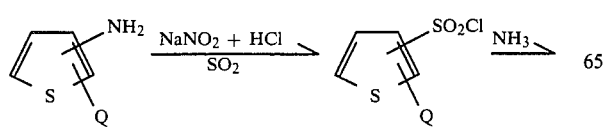

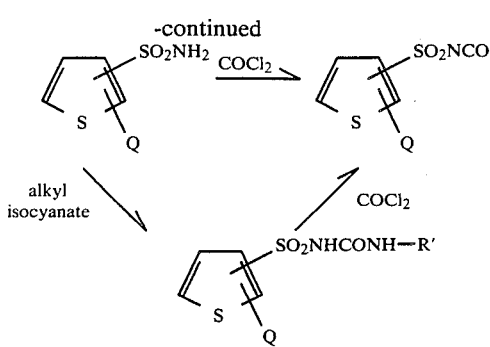

(wherein HAL is a halogen atom; Q is an ethenyl or propenyl group having all hydrogen atoms replaced by chlorine atoms and/or fluorine atoms; R' is an alkyl group such as methyl, ethyl, n-propyl, isopropyl, n-butyl, isobutyl, sec-butyl or tert-butyl).

Reaction conditions such as reaction temperature, reaction time, optional solvents and alkaline materials that are used for preparing the starting compounds may be properly selected from the conditions commonly used in the same type of reactions. Some of the novel thiophene compounds according to the present invention may also be produced by the following methods:

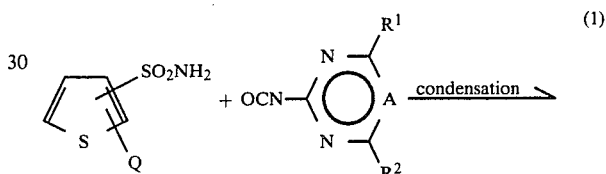

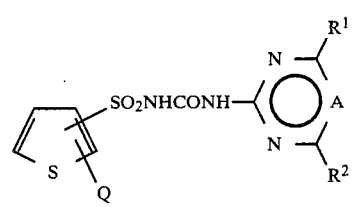

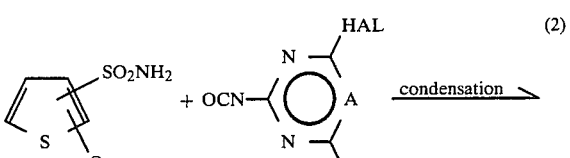

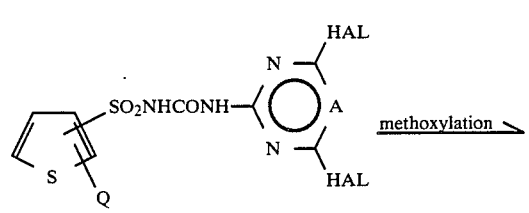

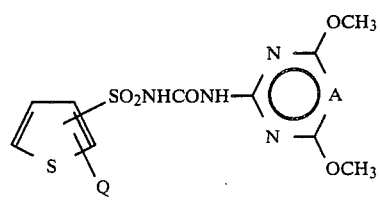

(wherein HAL is a halogen atom; A, Q, $R^1$ and $R^2$ are the same as defined above).

The specific methods for preparing several of the compounds according to the present invention are shown below.

PREPARATION EXAMPLE 1

Preparation of N-(4,6-dimethoxypyrimidin-2-yl)aminocarbonyl)-3-(1,2,3,3,3-pentafluoropropen-1-yl)-2-thiophenesulfonamide (1) N-tert-butyl-2-thiophenesulfomaide (6.5 g) was dissolved in 100 ml of tetrahydrofuran under nitrogen stream. To the solution, 32 ml of a 1.6M solution of n-butyllithium in n-hexane was added dropwise at 0°–10° C., followed by stirring for 1 hour. Thereafter, 5.56 g of trimethylsilyl chloride was added dropwise at 0°–5° C., and reaction was performed under stirring for 17 hours at room temperature. After completion of the reaction, the resulting product was poured into water, acidified with hydrochloric acid and extracted with ether. The extracted layer was washed with water and dried over anhydrous sodium sulfate. Ether was distilled off under vacuum, and the residue was purified by column chromatography on silica gel (eluent: methylene chloride). The resulting crystals were washed with n-hexane and dried to obtain 2.7 g of N-tert-butyl-5-trimethylsilyl-2-thiophenesulfonamide having a melting point of 102° to 104° C.

(2) Two grams of the N-tert-butyl-5-trimethylsilyl-2-thiophenesulfonamide prepared in (1) above was dissolved in 100 ml of dry ether under nitrogen stream. To the solution, 15 ml of a 1.6M solution of n-butyllithium in n-hexane was added dropwise at 10° to 15° C., followed by stirring at room temperature for 4 hours. Subsequently, a dry ice condenser was attached to the reactor, and then 10 g of hexafluoropropene was charged at 0° to 10° C. under nitrogen stream. Reaction was performed under stirring for 3 hours. After completion of the reaction, the resulting product was poured into water, acidified with hydrochloric acid and extracted with ether. The ether layer was washed with water and dried. After distilling off ether under vacuum, the residue was purified by column chromatography on silica gel (eluent: methylene chloride) to provide 1.6 g of N-tert-butyl-3-(1,2,3,3,3-pentafluoropropen-1-yl)-5-trimethylsilyl-2-thiophenesulfonamide having a melting point of 92° to 94° C.

(3) A portion (1.5 g) of the N-tert-butyl-3-(1,2,3,3,3-pentafluoropropen-1-yl)-5-trimethylsilyl-2-thiophenesulfonamide prepared in (2) was reacted with 4 ml of trifluoroacetic acid under stirring at room temperature for 13 hours. After completion of the reaction, the resulting product was poured into water and extracted with methylene chloride. The extracted layer was washed with water and dried. After distilling off methylene chloride under vacuum, the residue was purified by column chromatography on silica gel (eluent: methylene chloride) to provide 0.93 g of 3-(1,2,3,3,3-pentafluoropropen-1-yl)-5-trimethylsilyl-2-thiophenesulfonamide having a melting point of 129° to 140° C.

(4) One gram of the 3-(1,2,3,3,3-pentafluoropropen-1-yl)-5-trimethylsilyl-2-thiophenesulfonamide prepared in (3) was treated with 4 ml of trifluoromethanesulfonic acid under stirring at room temperature for 2 hours. After completion of the reaction, the resulting product was poured into water and extracted with methylene chloride. The extracted layer was washed with water and dried. After distilling off methylene chloride, the residue was purified by column chromatography on silica gel (eluent: methylene chloride) to provide 0.67 g of 3-(1,2,3,3,3-pentafluoropropen-1-yl)-2-thiophenesulfonamide having a melting point of 108° to 111° C.

(5) A portion (0.17 g) of the 3-(1,2,3,3,3-pentafluoropropen-1-yl)-2-thiophenesulfonamide prepared in (4) and 0.18 g of phenyl-N-(4,6-dimethoxypyrimidin-2-yl)carbamate were dissolved in 4 ml of dry acetonitrile. To the solution, 0.10 g of 1,8-diazabicyclo(5,4,0)-7-undecene was added dropwise, and the mixture was subjected to reaction under stirring for 2.5 hours at room temperature. After completion of the reaction, the resulting product was poured into water and acidified with hydrochloric acid. The precipitated crystals were filtered, washed with water and dried to obtain 0.210 g of the object compound having a melting point of 129° to 133° C.

PREPARATION EXAMPLE 2

Preparation of N-((4,6-dimethoxy-1,3,5-triazin-2-yl)aminocarbonyl)-3-(1,2,3,3,3-pentafluoropropen-1-yl)-2-thiophenesulfonamide According to steps (1) to (4) in Preparation Examples 1, 3-(1,2,3,3,3-pentafluoropropen-1-yl)-2-thiophenesulfonamide was prepared. A portion (0.3 g) of this substance and 0.311 g of phenyl-N-(4,6-dimethoxy-1,3,5-triazin-2-yl)carbamate were dissolved in 4 ml of dry acetonitrile. To the solution, 0.175 g of 1,8-diazabicyclo-(5,4,0)-7-undecene was added dropwise, and the mixture was subjected to reaction under stirring for 2.5 hours at room temperature. After completion of the reaction, the resulting product was poured into water and acidified with hydrochloric acid. The precipitated crystals were filtered, washed with water and dried to obtain 0.47 g of the object compound having a melting point of 149° to 153° C.

PREPARATION EXAMPLE 3

Preparation of N-((4,6-dimethoxypyrimidin-2-yl)aminocarbonyl)-3-(2-chloro-1,2-difluoroethenyl)-2-thiophenesulfonamide (1) N-tert-butyl-5-trimethylsilyl-2-thiophenesulfonamide was prepared according to step (1) in Preparation Example 1. A portion (1.6 g) of this substance was dissolved in 30 ml of dry ether under nitrogen stream. To the solution, 10.3 ml of a 1.6M solution of n-butyllithium in n-hexane was added dropwise at 0° to 10° C., followed by stirring for 1 hour. Then, the mixture was cooled to −30° C. Chlorotrifluoroethylene (7 g) was introduced into the reactor and subjected to reaction for 2 hours under stirring. Thereafter, the temperature of the reaction mixture gradually rised to room temperature, at which the reaction was continued overnight. After completion of the reaction, the resulting product was poured into water, acidified with hydrochloric acid and extracted with ether. The extracted layer was washed with water and dried. After distilling off ether under vacuum, the residue was purified by column chromatography on silica gel (eluent: methylene chloride/n-hexane=1/1) to provide 0.74 g of N-tert-butyl-3-(2-chloro-1,2-difluoroethenyl)-5-trimethylsilyl-2-thiophenesulfonamide having a melting point of 65° to 67° C.

(2) A portion (0.74 g) of the N-tert-butyl-3-(2-chloro-1,2-difluoroethenyl)-5-trimethylsilyl-2-thiophenesulfonamide prepared in (1) was treated with 4 ml of trifluoromethanesulfonic acid under stirring at room temperature for 2 hours. After completion of the reaction, the resulting product was poured into water and extracted with methylene chloride. The extracted layer was washed with water and dried. After distilling off methylene chloride under vacuum, the residual crystals were washed with a small amount of toluene and dried to obtain 0.26 g of 3-(2-chloro-1,2-difluoroethenyl)-2-thiophenesulfonamide having a melting point of 112° to 116° C.

(3) A portion (85 mg) of the 3-(2-chloro-1,2-difluoroethenyl)-2-thiophensulfonamide prepared in (2) and 113 mg of phenyl-N-(4,6-dimethoxypyrimidin-2-yl)carbamate were dissolved in 5 ml of dry acetonitrile. To the solution, 63 mg of 1,8-diazabicyclo(5,4,0)-7-undecene was added dropwise, and the mixture was subjected to reaction under stirring for 2 hours at room temperature. After completion of the reaction, the product was poured into water and acidified with hydrochloric acid. The precipitated crystals were filtered, washed with water and dried to obtain 100 mg of the object compound having a melting point of 168° to 172° C.

Specific examples of the substituted thiophenesulfonamide compound according to the present invention are listed below.

Compound No. 1: N-((4,6-dimethoxypyrimidin-2-yl)aminocarbonyl)-3-(1,2,3,3,3-pentafluoropropen-1-yl)-2-thiophenesulfonamide, mp 129°–133° C.

Compound No. 2: N-((4-methoxy-6-methylpyrimidin-2-yl)aminocarbonyl)-3-(1,2,3,3,3-pentafluoropropen-1-yl)-2-thiophenesulfonamide, mp 171°–175° C.

Compound No. 3: N-((4,6-dimethylpyrimidin-2-yl)aminocarbonyl)-3-(1,2,3,3,3-pentafluoropropen-1-yl)-2-thiophenesulfonamide, mp 142°–145° C.

Compound No. 4: N-((4,6-dimethoxypyrimidin-2-yl)aminocarbonyl)-2-(1,2,3,3,3-pentafluoropropen-1-yl)-3-thiophenesulfonamide, mp 183°–185° C.

Compound No. 5: N-((4,6-dimethoxy-1,3,5-triazin-2yl-)aminocarbonyl)-3-(1,2,3,3,3-pentafluoropropen-1-yl)-2-thiophenesulfonamide, mp 149°–153° C.

Compound No. 6: N-((4,5-dimethoxy-1,3,5-triazin-2-yl)aminocarbonyl)-2-(1,2,3,3,3-pentafluoropropen-1-yl)-3-thiophenesulfonamide, mp 160°–164° C.

Compound No. 7: N-((4-methoxy-6-methyl-1,3,5-triazin-2-yl)aminocarbonyl)-3-(1,2,3,3,3-pentafluoropropen-1-yl)-2-thiophenesulfonamide, mp 120°–124° C.

Compound No. 8: N-((4,6-dimethoxypyrimidin-2-yl)aminocarbonyl)-3-(1,2,2-trifluoroethenyl)-2-thiophenesulfonamide Compound No. 9: N-((4,6-dimethoxy-1,3,5-triazin-2-yl)-aminocarbonyl)-3-(2-chloro-1,2-difluoroethenyl)-2-thiophenesulfonamide, mp 136°–144° C.

Compound No. 10: N-((4-methoxy-6-methyl-1,3,5-triazin-2-yl)aminocarbonyl)-3-(2-chloro-1,2-difluoroethenyl)-2-thiophenesulfonamide, mp 64°–69° C.

Compound No. 11: N-((4,6-dimethoxypyrimidin-2-yl)aminocarbonyl)-3-(2-chloro-1,2-difluoroethenyl)-2-thiophenesulfonamide, mp 168°–172° C.

Compound No. 12: N-((4,6-dimethylpyrimidin-2-yl)aminocarbonyl)-3-(2-chloro-1,2-difluoroethenyl)-2-thiophenesulfonamide, mp 155°–157° C.

Compound No. 13: N-((4,6-dimethoxypyrimidin-2-yl)aminocarbonyl)-2-(2-chloro-1,2-difluoroethenyl)-3-thiophenesulfonamide, mp 172°–175° C.

The object compounds of the present invention include cis- and trans-stereoisomers thereof.

The substituted thiophenesulfonamide compounds and salts thereof according to the present invention exhibit excellent herbicidal activity when they are used as the active ingredient of herbicides. The compounds and salts thereof are particularly effective in selective and low-dose weed control in crops. The compounds and salts thereof are suitable for use as herbicides in paddy fields since they are effective even on weeds that have gone into the high stage of growth. The compounds and salts thereof are also capable of controlling weeds in upland fields.

Herbicides containing the compounds and salts thereof according to the present invention as the active ingredient will find many other applications such as orchards, mulberry fields, forests, farm roads, playgrounds and factory sites. The herbicides may be applied either as a soil treatment or as a foliar treatment.

The herbicides containing the compounds or salts thereof according to the present invention as the active ingredient can be formulated into various forms such as granules, wettable powder, emulsifiable concentrate or liquids by usually incorporating carriers, and optionally mixing with other agriculturally acceptable adjuvants such as diluents, solvents, emulsifiers, extenders and surfactants. The suitable weight ratio of the active ingredient compound to the agriculturally acceptable adjuvant generally ranges from 0.05:99.95 to 90:10, preferably from 0.1:99.9 to 60:40. The suitable dose of the active ingredient compound may vary with weather conditions, soil, type of the formulation, target weed and the timing of application. As a guide, the active ingredient compound is generally used in 0.1 to 100 g, preferably 0.5 to 50 g, per are.

The herbicide according to the present invention can also be mixed or used together with suitable materials such as other pesticides, fertilizers, soil or softenr, and it often occurs that the activities of the herbicide are enhanced by such combined use. The herbicide according to the present invention may of course be mixed or used together with other herbicides which may contain the following compounds as the active ingredient:

2,4-dichlorophenyl-3'-methoxy-4'-nitrophenyl ether, 2,4-dichlorophenyl-3'-methoxycarbonyl-4'-nitrophenyl ether, 2-chloro-2',6'-diethyl-N-(butoxymethyl)acetanilide, 2-chloro-2',6'-diethyl-N-(propoxyethyl)acetanilide, 4-ethoxymethoxybenz-2',3'-dichloroanilide, S-(2-methyl-1-piperidyl-carbonylmethyl)-O,O-di-n-propyl-dithiophosphate, S-(4-chlorobenzyl)-N,N-diethylthiol carbamate, S-ethyl-hexahydro-1H-azepin-1-carbothioate, S-(1-methyl-1-phenethyl)piperidine-1-carbothioate, O,O-diisopropyl-S-(2-benzenesulfonylaminoethyl)phosphorodithioate, 5-tert-butyl-3-(2,4-dichloro-5-isopropoxyphenyl)-1,3,4-oxadiazolin-2-one, 2-(benzothiazol-2-yloxy)-N-methylacetanilide, O-ethyl-O-(3-methyl-6-nitrophenyl)-sec-butylphosphoroamidothioate, 4-(2,4-dichlorobenzoyl)-1,3-dimethyl-5-phenacyloxypyrazole, 4-(2,4-dichlorobenzoyl)-1,3-dimethylpyrazol-5-yl-p-toluenesulfonate, 4-(2,4-dichloro-3-methylbenzoyl)-1,3-dimethyl-5-phenacyloxypyrazole, 4-amino-6-tert-butyl-3-methylthio-1,2,4-triazin-5(4H)-one, 2-(2-chloro-4-ethylamino-S-triazin-6-ylamino)-2-methylpropionitrile, 2-chloro-4-ethylamino-6-isopropylamino-S-triazine, 3-(3,4-dichlorophenyl)-1-methoxy-1-methylurea, n-butyl$\alpha$-[4-(5-trifluoromethyl-2-pyridyloxy)phenoxy]propionate, methyl $\alpha$-[4-(2,4-dichlorophenoxy)phenoxy]propionate, 2-[1-(ethoxyimino)butyl]-5-(2-ethylthiopropyl)-3-hydroxy-2-cyclohexen-1-one, 3,4-dimethyl-2,6-dinitro-N-1-ethylpropylaniline, $\alpha,\alpha,\alpha$-trifluoro-2,6-dinitro-N,N-dipropyl-p-toluidine, 2-chloro-2',6'-diethyl-N-(methoxymethyl)acetanilide, 2-chloro-N-(2-ethyl-6-methylphenyl)-N-(2-methoxy-1-methylethyl)acetamide, 2-methoxy-3,6-dichlorobenzoic acid dimethylamine, 2-sec-butyl-4,6-dinitrophenol, S-ethyl-N,N-di-n-propylthiol carbamate and S-ethyl-N,N-dibutylthiol carbamate.

Tests were conducted to examine the herbicidal activity of the compounds or salts thereof according to the present invention. Test procedures and the results obtained are shown below.

TEST EXAMPLE 1

A plurality of 1/2,000 are pots were provided and each was charged with soil from a paddy field. Predetermined amounts of seeds of umbrella plant (*Cyperus difformis* L.), ducktongue weed (monochoria) (*Monochoria vaginalis* Presl), bulrush (*Scirpus juncoides* Roxb.) and *Lindernia spp.* as well as tubers of Japanese ribbon wapato (*Sagittaria pygmaea* Miq.) were sown and held under a wet condition.

When the bulrush (*Scirpus juncoides* Roxb.) grew to one leaf stage, each pot was flooded to a water depth of about 5 cm. Wettable powders containing the compounds listed in Table 1 were diluted with water and pipetted into the pots in predetermined amounts. Twenty-one days after the application, each weed control was determined by visual evaluation on a scale of 1 to 5. The results are shown in Table 1.

Index of rating:
5 ... complete withering of the weed
1 ... weed as vigorous as in the untreated check each pot was puddled and two rice plants (*Oryzae sativa* L., variety: "Nihon-bare") of 2.5 leaf stage were transplanted. Four days after the transplantation, wettable powders containing the compounds listed in Table 2 were diluted with water and pipetted into the pots in predetermined amounts. Thirty days after the application, the rice growth was determined by visual evaluation on the same scale as used in Test Example 1. The results are shown in Table 2.

TABLE 2

| Compound No. | Active Ingredient (g/a) | Rice Growth Inhibition |
| --- | --- | --- |
| 1 | 5 | 1 |
| 2 | 5 | 2 |
| 3 | 5 | 1 |
| 4 | 5 | 1 |
| 5 | 5 | 1 |
| 6 | 5 | 1 |
| 7 | 5 | 1 |
| 9 | 5 | 2 |
| 10 | 5 | 1 |
| 11 | 5 | 2 |

TEST EXAMPLE 3

The procedure of Test Example 1 was repeated except that seeds of another weed, barnyardgrass (*Echinochloa oryzicola* Vasing.) were also sown, two rice plants (*Oryza sativa* L., variety: "Nihon-bare") of a 2.5-leaf stage were transplanted per pot, and that the pots were

TABLE 1

| Compound No. | Active Ingredient (g/a) | *Cyperus difformis* L. | *Monochoria vaginalis* Presl | *Scirpus juncoides* Roxb. | *Lindernia* spp. | *Sagittaria pygmaea* Miq. |
| --- | --- | --- | --- | --- | --- | --- |
| 1 | 2.5 | 5 | 5 | 5 | 5 | 5 |
|   | 1.25 | 5 | 5 | 5 | 5 | 5 |
| 2 | 2.5 | 5 | 5 | 5 | 5 | 5 |
|   | 1.25 | 5 | 5 | 5 | 5 | 5 |
| 3 | 2.5 | 5 | 5 | 5 | 5 | 5 |
|   | 1.25 | 5 | 5 | 5-4 | 5 | 5 |
| 4 | 2.5 | 5 | 5 | 5-4 | 5 | 5 |
|   | 1.25 | 5 | 5 | 3 | 5 | 5 |
| 5 | 2.5 | 5 | 5 | 5 | 5 | 5 |
|   | 1.25 | 5 | 5 | 5 | 5 | 5 |
| 6 | 2.5 | 5 | 5 | 5 | 5 | 5 |
|   | 1.25 | 5 | 5 | 4-5 | 5 | 5 |
| 7 | 2.5 | 5 | 5 | 5-4 | 5 | 5 |
|   | 1.25 | 5 | 5 | 4-5 | 5 | 5 |
| 9 | 2.5 | 5 | 5 | 5 | 5 | 5 |
|   | 1.25 | 5 | 5 | 5 | 5 | 5 |
| 10 | 2.5 | 5 | 5 | 5 | 5 | 5 |
|   | 1.25 | 5 | 5 | 5-4 | 5 | 5 |
| 11 | 2.5 | 5 | 5 | 5 | 5 | 5 |
|   | 1.25 | 5 | 5 | 5 | 5 | 5 |
| 12 | 2.5 | 5 | 5 | 5 | 5 | 5 |
|   | 1.25 | 5 | 5 | 5 | 5 | 5 |
| 13 | 2.5 | 5 | 5 | 5 | 5 | 5 |
|   | 1.25 | 5 | 5 | 5 | 5 | 5 |

TEST EXAMPLE 2

A plurality of 1/5,000 are pots were provided and each was charged with soil from a paddy field. After irrigation with a suitable amount of water, the soil in treated with the compounds listed in Table 3. The results of Test Example 3 are shown in Table 3. The parenthesized figure following each compound name represents its amount in g/a as the active ingredient.

TABLE 3

| Test Compound | | Barnyardgrass | Bulrush | Umbrella plant | Japanese ribbon wapato | Ducktongue weed | *Lindernia* spp. | Rice |
| --- | --- | --- | --- | --- | --- | --- | --- | --- |
| No. 1 + A | (0.75) (4.5) | 5 | 5 | 5 | 5 | 5 | 5 | 1 |
| No. 1 + B | (0.75) (12) | 5 | 5 | 5 | 5 | 5 | 5 | 1 |

TABLE 3-continued

| Test Compound | | Barnyard-grass | Bulrush | Umbrella plant | Japanese ribbon wapato | Ducktongue weed | Lindernia spp. | Rice |
|---|---|---|---|---|---|---|---|---|
| No. 2 + A | (0.75) (4.5) | 5 | 5 | 5 | 5 | 5 | 5 | 1 |
| No. 2 + B | (0.75) (12) | 5 | 5 | 5 | 5 | 5 | 5 | 1 |
| No. 5 + A | (0.75) (4.5) | 5 | 5 | 5 | 5 | 5 | 5 | 1 |
| No. 5 + C | (0.75) (12) | 5 | 5 | 5 | 5 | 5 | 5 | 1 |
| No. 6 + A | (0.75) (4.5) | 5 | 5 | 5 | 5 | 5 | 5 | 1 |
| No. 6 + C | (0.75) (4.5) | 5 | 5 | 5 | 5 | 5 | 5 | 1 |
| No. 9 + D | (0.6) (20) | 5 | 5 | 5 | 5 | 5 | 5 | 1 |
| No. 10 + A | (0.6) (4.5) | 5 | 5 | 5 | 5 | 5 | 5 | 1 |
| No. 11 + E | (0.6) (20) | 5 | 5 | 5 | 5 | 5 | 5 | 1 |

Note: Compounds A to E in Table 3 are as follows:
Compound A: 2-chloro-2',6'-diethyl-N—(propoxyethyl)acetanilide
Compound B: 2-(benzothiazol-2-yloxy)-N—methylacetamide
Compound C: 2-chloro-2',6'-diethyl-N—(butoxymethyl)acetanilide
Compound D: S—(4-chlorobenzyl)-N,N—diethylthiol carbamate
Compound E: S—(1-methyl-1-phenethyl)piperidine-1-carbothioate.

TEST EXAMPLE 4

The procedure of Test Example 3 was repeated except that pots were treated with the compounds listed in Table 4 when barnyardgrass reached a two-leaf stage. The results are shown in Table 4. The parenthesized figure following each compound name represents its amount in g/a as the active ingredient.

TABLE 4

| Test Compound | | Barnyard-grass | Bulrush | Umbrella plant | Japanese ribbon wapato | Ducktongue weed | Lindernia spp. | Rice |
|---|---|---|---|---|---|---|---|---|
| No. 1 + F | (1) (20) | 5 | 5 | 5 | 5 | 5 | 5 | 1 |
| No. 1 + D | (1) (20) | 5 | 5 | 5 | 5 | 5 | 5 | 1 |
| No. 2 + F | (1) (20) | 5 | 5 | 5 | 5 | 5 | 5 | 1 |
| No. 2 + D | (1) (20) | 5 | 5 | 5 | 5 | 5 | 5 | 1 |
| No. 3 + G | (1) (10) | 5 | 5 | 5 | 5 | 5 | 5 | 1–2 |
| No. 5 + F | (1) (20) | 5 | 5 | 5 | 5 | 5 | 5 | 1 |
| No. 5 + G | (1) (10) | 5 | 5 | 5 | 5 | 5 | 5 | 1 |
| No. 6 + F | (1) (20) | 5 | 5 | 5 | 5 | 5 | 5 | 1 |
| No. 6 + G | (1) (10) | 5 | 5 | 5 | 5 | 5 | 5 | 1–2 |
| No. 11 + D | (1) (20) | 5 | 5 | 5 | 5 | 5 | 5 | 1–2 |

Note: Compound D in Table 4 is the same as defined for Table 3, and compounds F and G are as follows:
Compound F: S—ethyl-hexahydro-1H—azepin-1-carbothioate
Compound G: S—(2-methyl-1-piperidyl-carbonylmethyl)-0,0-di-n-propyl dithiophosphate.

TEST EXAMPLE 5

A plurality of 1/1,000 are pots were provided, charge with soil from an upland farm, and sown with seeds of cocklebur (*Xanthium strumarium* L.), morningglory (*Ipomoea purpurea* Roth), prickly sida (*Sida spinosa* L.), smartweed (*Polygonum lapathiofolium* L.) and pigweed (*Amaranthus viridis* L.). When the weeds reached certain growth stages (three-leaf stage for cockebur, 1.5-leaf stage for morningglory, one leaf stage for prickly sida, two-leaf stage for smartweed, and one-leaf stage for pigweed), wettable powders containing the compounds of the present invention as active ingredients in the amounts listed in Table 5 were applied foliarly to the respective weeds. The wettable powders were applied after being diluted with 5,000 ml/a of water. Thirty days after the application, each weed control was determined by visual evaluation on a scale 1 to 10. The results are shown in Table 5.

Index of rating:

10 ... complete control
1 ... weed as vigorous as in the untreated check

TABLE 5

| Compound No. | Active Ingredient (g/a) | Degree of Growth Inhibition | | | | |
|---|---|---|---|---|---|---|
| | | Cocklebur | Morning-glory | Prickly Sida | Smart-weed | Pig-weed |
| 1 | 10 | 10 | 10 | 6 | 6 | 10 |
|   | 5  | 10 | 10 | 6 | 6 | 9  |
| 2 | 10 | 10 | 9  | 9 | 7 | 9  |
|   | 5  | 10 | 9  | 7 | 6 | 8  |

TABLE 5-continued

| Compound No. | Active Ingredient (g/a) | Degree of Growth Inhibition | | | | |
|---|---|---|---|---|---|---|
| | | Cocklebur | Morning-glory | Prickly Sida | Smartweed | Pigweed |
| 11 | 10 | 10 | 10 | 8 | 7 | 9 |
| | 5 | 10 | 10 | 8 | 7 | 8 |

TEST EXAMPLE 6

A plurality of 1/1,000 are pots were provided, charged with soil from an upland farm, and sown with seeds of cocklebur (*Xanthium strumarium* L.), morning-glory (*Ipomoea purpurea* Roth), prickly sida (*Sida spinosa* L.), smartweed (*Polygonum lapathiofolium* L.) and pigweed (*Amaranthus viridis* L.). The seeds were covered with soil to a thickness of about 1 cm. On the next day, wettable powders containing Compound Nos. 5 and 6 of the present invention as active ingredients in 20 g/a were uniformly sprayed onto the soil surface after the powders were diluted with 15 liters per are of water. Thirty days after the application, each weed control was determined by visual evaluation on the same scale as in Test Example 5. The results are shown in Table 6.

TABLE 6

| Compound No. | Active Ingredient (g/a) | Degree of Growth Inhibition | | | | |
|---|---|---|---|---|---|---|
| | | Cocklebur | Morning-glory | Prickly Sida | Smartweed | Pigweed |
| 5 | 20 | 10 | 10 | 10 | 10 | 10 |
| 6 | 20 | 10 | 9 | 9 | 10 | 10 |

Some typical examples of herbicidal formulations containing the compounds according to the present invention are shown below.

FORMULATION EXAMPLE 1

| (1) | Bentonite | 40 parts by wt. |
|---|---|---|
| (2) | Calcium carbonate | 57.95 parts by wt. |
| (3) | Calcium lignin sulfonate | 2 parts by wt. |
| (4) | Compound No. 11 | 0.05 part by wt. |

The four ingredients listed above were blended with a suitable amount of water and the mixture was granulated to form a granule.

FORMULATION EXAMPLE 2

| (1) | Bentonite | 40 parts by wt. |
|---|---|---|
| (2) | Clay | 57.5 parts by wt. |
| (3) | Calcium lignin sulfonate | 2 parts by wt. |
| (4) | Compound No. 1 | 0.5 part by wt. |

The four ingredients listed above were blended with a suitable amount of water and the mixture was granulated to form a granule.

FORMULATION EXAMPLE 3

| (1) | Jeeklite (trade name for kaolinite, produced by Jeeklite Co.) | 67 parts by wt. |
|---|---|---|
| (2) | Carplex (trade name for produced by Shionogi & Co., Ltd.) fine silicon dioxide (white carbon) | 8 parts by wt. |
| (3) | Sorpol 5039 (trade name for produced by Toho Chemical Co., Ltd.) mixture of polyoxyethylene alkylarylether sulfate and fine silicon dioxide (50:50) | 3 parts by wt. |
| (4) | Lavelin FAN (trade name for produced by Daiichi Kogyo Seiyaku Co, Ltd.) sodium naphthalene sulfonate-formalin | 2 parts by wt. |
| (5) | Compound No. 1 | 20 parts by wt. |

The ingredients listed above were mixed to form a wettable powder.

FORMULATION EXAMPLE 4

| (1) | Jeeklite | 8 parts by wt. |
|---|---|---|
| (2) | Carprex | 15 parts by wt. |
| (3) | Sorpol 5039 (trade name for produced by Toho Chemical Co., Ltd.) | 4 parts by wt. |
| (4) | Lavelin FAN | 3 parts by wt. |
| (5) | Compound No. 5 | 70 parts by wt. |

The ingredients listed above were mixed to form a wettable powder.

FORMULATION EXAMPLE 5

| (1) | Xylene | 67 parts by wt. |
|---|---|---|
| (2) | N—methyl-2-pyrrolidone | 20 parts by wt. |
| (3) | Sorpol 3005X (trade name for produced by Toho Chemical Co., Ltd.) polyoxyethylene styrylphenylether | 8 parts by wt. |
| (4) | Compound No. 11 | 5 parts by wt. |

The ingredients listed above were mixed uniformly under agitation to form an emulsifiable concentrate.

FORMULATION EXAMPLE 6

| (1) | Water | 93.5 parts by wt. |
|---|---|---|
| (2) | Sodium hydroxide | 1 part by wt. |
| (3) | Emulgen PP-150 (trade name for produced by Kao Soap Co., Ltd.) | 0.5 part by wt. |
| (4) | Compound No. 11 | 5 parts by wt. |

The ingredients listed above were mixed uniformly under agitation to form an emulsifiable concentrate.

While the invention has been described in detail and with reference to specific embodiments thereof, it will be apparent to one skilled in the art that various changes and modifications can be made therein without departing from the spirit and scope thereof.

What is claimed is:

1. A thiophenesulfonamide compound of the formula:

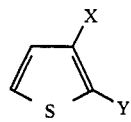

wherein either one of X and Y is an ethenyl or propenyl group having all hydrogen atoms replaced by chlorine atoms and/or fluorine atoms, and the other is group

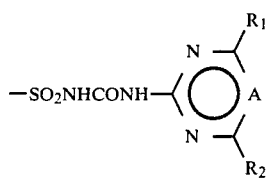

(wherein $R_1$ and $R_2$ are each a methyl or methoxy group, and A is =CH—) or agriculturally suitable salt thereof.

2. A thiophenesulfonamide compound or agriculturally suitable salt thereof according to claim 1 wherein X is an ethenyl or propenyl group having all hydrogen atoms replaced by chlorine atoms and/or fluorine atoms, and Y is the group

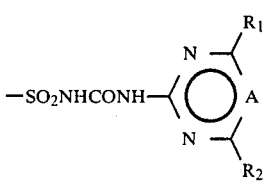

(wherein $R_1$ and $R_2$ are each a methyl or methoxy group; and A is =CH—).

3. A substituted thiophenesulfonamide compound or a salt thereof according to claim 1 wherein either one of X and Y is a 1,2,3,3,3-pentafluoro-1-propenyl group, and the other is the group

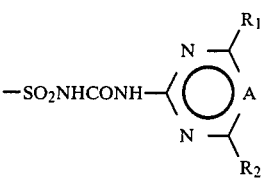

(wherein $R_1$ and $R_2$ are each a methyl or methoxy group; and A is =CH—).

4. A thiophenesulfonamide compound or a salt thereof according to claim 1 wherein either one of X and Y is a 2-chloro-1,2-difluoroethenyl group, and the other is the group

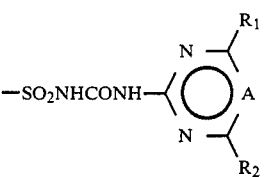

(wherein $R_1$ and $R_2$ is a methyl or methoxy group; and A is =CH—).

5. A thiophenesulfonamide compound or a salt thereof according to claim 1 wherein X is an ethenyl or propenyl group having all hydrogen atoms replaced by chlorine atoms and/or fluorine atoms, and Y is the group

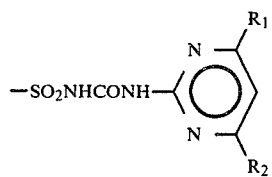

(wherein $R_1$ and $R_2$ are each a methyl or methoxy group).

6. A thiophenesulfonamide compound or a salt thereof according to claim 1 wherein X is a 1,2,3,3,3-pentafluoro-1-propenyl or 2-chloro-1,2-difluoroethenyl group, and Y is the group

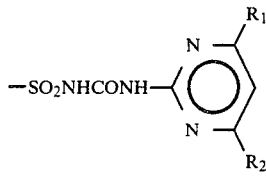

(wherein $R_1$ and $R_2$ are each a methyl group or methoxy group).

7. A thiophenesulfonamide compound or a salt thereof according to claim 1 wherein said compound is N-((4,6-dimethoxypyrimidin-2-yl)aminocarbonyl)-3-(1,2,3,3,3-pentafluoropropen-1-yl)-2-thiophenesulfonamide.

8. A thiophenesulfonamide compound or a salt thereof according to claim 1 wherein said compound is N-((4,6-dimethoxypyrimidin-2-aminocarbonyl)-3-(2-chloro-1,2-difluoroethenyl)-2-thiophenesulfonamide.

9. A herbicidal composition comprising a herbicidally effective amount of the thiophenesulfonamide compound or an agriculturally suitable salt thereof as recited in claim 1 and an agriculturally acceptable adjuvant.

10. A herbicidal composition according to claim 9 wherein the thiophenesulfonamide compound is mixed with the agriculturally acceptable adjuvant in a ratio ranging from 0.05:99.95 to 90:10 by weight.

11. A herbicidal composition comprising a herbicidally effective amount of the thiophenesulfonamide compound or an agriculturally suitable salt thereof as recited in claim 6 and an agriculturally acceptable adjuvant.

12. A herbicidal composition according to claim 11 wherein the thiophenesulfonamide compound is mixed with the agriculturally acceptable adjuvant in a ratio ranging from 0.05:99.95 to 90:10 by weight.

* * * * *